United States Patent [19]

Mitsui et al.

[11] Patent Number: 4,735,777

[45] Date of Patent: Apr. 5, 1988

[54] INSTRUMENT FOR PARALLEL ANALYSIS OF METABOLITES IN HUMAN URINE AND EXPIRED AIR

[75] Inventors: Yasuhiro Mitsui, Fuchu; Osami Okada, Chofu, both of Japan

[73] Assignee: Hitachi, Ltd., Tokyo, Japan

[21] Appl. No.: 828,623

[22] Filed: Feb. 12, 1986

[30] Foreign Application Priority Data

Mar. 11, 1985 [JP] Japan ..................... 60-46524

[51] Int. Cl.⁴ .................... G01N 30/02; G01N 1/22; A61B 5/00

[52] U.S. Cl. ........................ 422/70; 422/84; 128/630; 128/716; 128/719; 128/730; 73/61.1 C

[58] Field of Search ............... 422/70, 84; 128/630, 128/632, 633, 716, 718, 719, 730; 73/61.1 C

[56] References Cited

FOREIGN PATENT DOCUMENTS 0027062 2/1983 Japan ..................... 422/70

OTHER PUBLICATIONS

Sodal et al., "A High Performance Miniature Mass Spectrometer for Respiratory Gas Analysis", May 1-3, 1972, pp. 21-24.
Krotoszynski et al., "Characterization of Human Expired Air: A Promising Investigative and Diagnostic Technique", J. Chrm. Sc., vol. 15, 7/77, 239-244.
Rooth et al., "Acetone in Alveolar Air, and the Control of Diabetes", The Lancet, 11/19/66, 1102-1105.
Jansson et al., "Analysis of Organic Compounds in Human Breath by Gas Chromatography-Mass Spectrometry", J. Lab. & Clin. Med., 12/69, 961-5.
Teranishi et al., "Gas Chromatography of Volatiles From Breath and Urine", Anal. Chem., vol. 44, No. 1, 1/72, 18-19.
Levey et al., "Studies of Metabolic Products in Expired Air, II Acetone", J. Lab. & Clin. Med., 4/64, 574-583.
Lovett et al., "Real-Time Analysis of Breath Using an Atmos. Press. Ion. Mass Spect.", Biomed. Mass Spect., vol. 6, No. 3, 91-97, 1979.
Rhodes et al., "Metabolic Abnorm. Assoc. w/Diab. Mell., as Invest. by Gas Chr. & Pattern-Recog. Anal. of Prof. of vol. Metab.", Clin. Chem., vol. 27, No. 4, 1981.
Manolis, "The Diagnostic Potential of Breath Analysis", Clin. Chem., vol. 29, No. 1, 1983.

Primary Examiner—Michael S. Marcus
Assistant Examiner—Floyd E. Bennett, Jr.
Attorney, Agent, or Firm—Antonelli, Terry & Wands

[57] ABSTRACT

An apparatus for measuring metabolites contained in human expired air and for measuring metabolites contained in human urine and for extracting a correlation between the metabolite data in the expired air and the metabolite data in the urine is suitable for parallel analysis of the metabolites in human urine and expired air. An atmospheric pressure ionization mass spectrometer is suitable for measuring metabolites in the expired air. By storing reference data showing the relation between the metabolites in the expired air and those in the urine and, by comparing such data with a subject's metabolite data in the expired air and the metabolite data in the urine, abnormality of a subject can be detected.

15 Claims, 6 Drawing Sheets

ововоinstrument for parallel analysis of metabolites in human urine and expired air

INSTRUMENT FOR PARALLEL ANALYSIS OF METABOLITES IN HUMAN URINE AND EXPIRED AIR

BACKGROUND OF THE INVENTION

This invention relates to an apparatus for measuring metabolites in living bodies. More particularly, this invention concerns an apparatus for parallel analysis of metabolites in human urine and expired air by a non-invasive method suitable for obtaining information effective for diagnosis and elucidation of metabolism by simultaneously mesuring metabolites in the expired air and urine.

As a means for executing a health examination and elucidating metabolism in human bodies, there is measurment of metabolites. As a sample, blood is generally used, but there are defects in that the sampling of blood puts a burden on subjects and further continuous measurement on the same subject is impossible. In contrast, non-invasive measurement of metabolites using as a sample urine or expired air naturally excreted from a human body or the gas diffused from the skin can reduce the burden on the subjects. But since the metabolism of the human body is very complicated, it is important to effect judgement based on not a single information but rather on a plurality of information in order to give a clearer diagnosis.

Heretofore, as to the urine, various components such as proteins, saccharides, vitamins, etc. in the urine are measured and used for practical clinical laboratory tests.

As to metabolites in the expired air, since the amounts thereof are very trace (usually the level of ppb or less) and the measurement is very difficult, there are only a few reports which detect organic substances in the expired air, for example, B. Krotoszynski, G. Gabriel, H. O'Neill, and M. P. A. Claudio: J. Chromatographic Sci. vol. 15, pp. 239-244 (1977).

According to known non-invasive metabolite measuring methods, urine and expired air are measured independently. Particularly, since the detection of metabolites in the expired air is difficult, there has been no report as to the simultaneous measurement of metabolites in the urine and metabolites in the expired air. Therefore, no study has been made on the relationship between the metabolism as to the urine and that as to the expired air, which relationship can be a basis for clearer diagnosis and more suitable thereby based on a plurality of information and non-invasive sampling.

SUMMARY OF THE INVENTION

It is an object of this invention to provide an apparatus for parallel analysis of metabolites in human urine and expired air for measuring metabolites in the expired air and metabolites in the urine at the same time and for obtaining information on the metabolites from different metabolic routes.

It is another object of this invention to provide an apparatus for parallel analysis of metabolites in human urine and expired air in order to make it possible to detect an abnormality of a subject based on the correlation between the metabolites in the expired air and the metabolites in the urine.

This invention provides an apparatus for parallel analysis of metabolites in human urine and expired air comprising a means for measuring expired air to determine metabolites contained in the expired air, a means for measuring urine to determine metabolites in the urine simultaneously sampled with the expired air, and a means for extracting the correlation between the metabolites in the expired air and the metabolites in the urine from metabolite data determined by the expired air measuring means and metabolite data determined by the urine measuring means.

This invention also provides an apparatus for parallel analysis of metabolites in human urine and expired air comprising a means for measuring expired air to determine metabolites contained in the expired air from a subject, a means for measuring urine to determine metabolites in the urine from the subject simultaneously sampled with the expired air, a means for storing data showin the relation between the metabolites in the expired air and the metabolites in the urine, and a means for detecting an abnormality of the subject by comparing the relation between metabolite data in the expired air determinied by the expired air measuring means and metabolite data in the urine determined by the urine measuring means with the data showing the relation between the metabolites in the expired air and the metabolites in the urine stored in the storing means.

As the expired air measuring means, it is effective to use an atmospheric pressure ionization mass spectrometer comprising an ion source for ionizing an expired air sample under an atmospheric pressure, a high vacuum portion wherein a mass analyzer and an ion collector are installed, and an intermediate pressure portion placed between the ion source and the high vacuum portion.

DETAILED DESCRIPTION OF THE PREFERRED EMBODIMENTS

Figure 1:
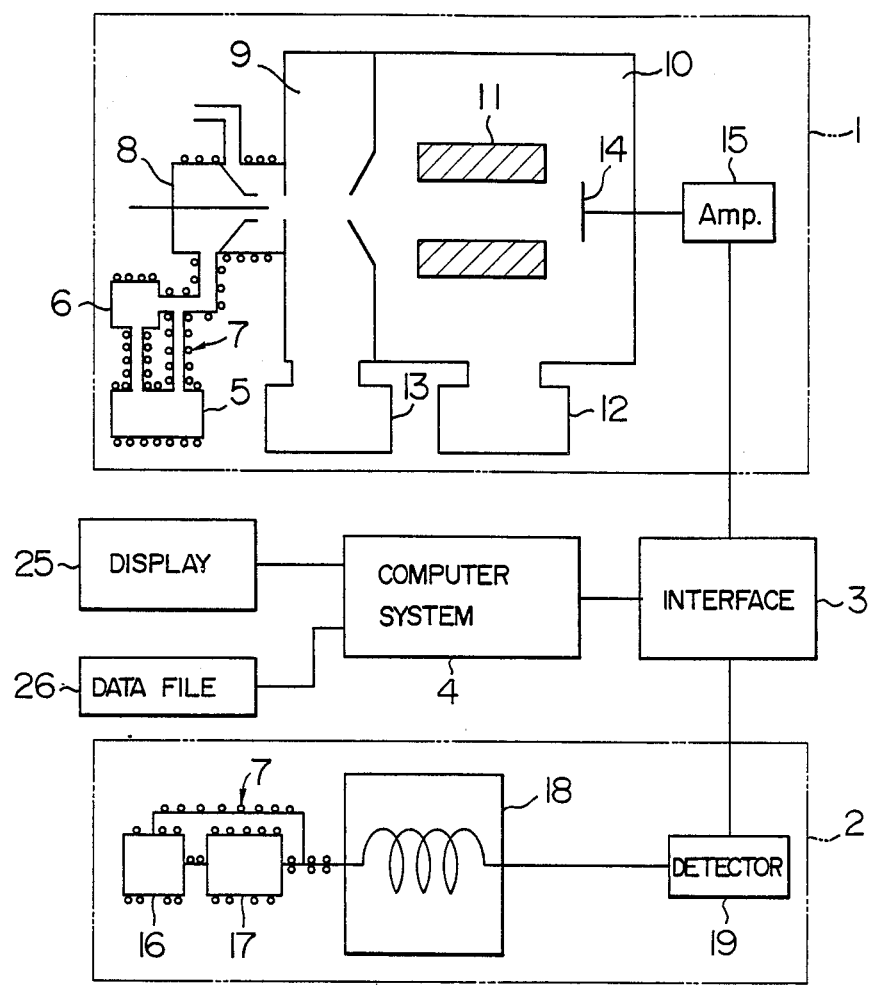
FIG. 1 is a schematic diagram showing one example of the apparatus for parallel analysis of metabolites in human urine and expired air according to this invention.

This invention is illustrated referring to the drawings.

FIG. 1 shows one example of the apparatus for parallel analysis of metabolites in human expired air and urine according to this invention, wherein an atmospheric pressure ionization mass spectrometer 1 and a liquid chromatograph 2 are connected to a computer system 4 via an interface 3. Trace amounts of metabolites in the expired air are measured by the atmospheric pressure ionization mass spectrometer 1 and amounts of metabolites in the urine are measured by the liquid chromatograph 2.

The atmospheric pressure ionization mass spectrometer 1 contains a mouthpiece or a sampling vessel 5 for sampling expired air. When the expired air is sampled on-line, the mouthpiece is used, while when sampled off-line, a bag containing the expired air is attached to the sampling vessel 5. The expired air sampled by the sampling vesel 5 is introduced to an ion source 8 directly or via an expired air sample concentrating device 6. The expired air sample concentrating device 6 is constructed, for example, to contain an absorbent for absorbing the metabolites in the expired air inside thereof, the absorbent being heated so as to release the metabolites when a high metabolite concentration is attained. Those ionized by the ion source 8 are introduced into an analyzing portion 10 which is a high vacuum portion via an intermediate pressure portion 9 and the ions are mass separated by a quadrapole mass analyzer 11 and detected at an ion collector 14, wherein the metabolites in the expired air is determined. The ion current proportional to the quantity of metabolites and obtained in the collector 14 is transmitted to the interface 3 via an amplifier 15. The intermediate pressure portion 9 and the high vacuum portion 10 are maintained at the predetermined pressure by vacuum pumps 13, 12, respectively.

In the liquid chromatograph 2 for detecting the metabolites in the urine, a urine sample from a urine sampling vessel 16 is introduced to a liquid chromatograph separation column 18 directly or via a urine sample concentrating device 17. The sample passed the column 18 is transmitted to a liquid chromatograph detector 19 to determine the metabolites in the urine. The output of the detector 19 is transmitted to the interface 3.

Using the above-mentioned apparatus, the expired air sample and the urine sample obtained from the same subject at the same time can be analyzed at the same time, that is, the expired air is analyzed by the atmospheric pressure ionization mass spectrometer 1 and the urine is analyzed by the liquid chromatograph 2. The atmospheric pressure ionization mass spectrometer 1 is very sensitive (ppt level) to gaseous samples, and thus enables detection of trace amount of volatile metabolites contained in the expired air. The liquid chromatograph 2 enables detection of non-volatile high molecular weight metabolites contained in the urine. In order to pass the expired air sample to the ion source 8, an expired air sampling device or an expired air sample introducing device 5 is combined to the atmospheric pressure ionization mass spectrometer 1. In the case of on-line sampling wherein the expired air sample from a subject is directly passed to the ion source 8, the mouthpiece and the ion source 8 are combined by a sample introducing pipe. On the other hand, in the case of off-line sampling wherein a subject and the apparatus are positioned with a long distance, an expired air sampling vessel (e.g. a bag made of a plastic film) can be attached to the apparatus. In the case of a urine sample, a urine sampling device or a urine sample introducing device 16 is combined to the liquid chromatograph 2 similarly. The sampling device or the introducing device for the expired air sample or urine sample can be equipped with a heating means 7 for providing variable temperatures in order to prevent the inner surface of the introducing pipe or the sampling vessel from the adsorption of the sample which is in a trace amount. In the case of measuring ultra-trace amounts of metabolites which cannot be measured by the atmospheric pressure ionization mass spectrometer and the liquid chromatograph, a sample concentrating means 6 and 17 can be provided in a proper portion of the introducing pipe.

Figure 2:
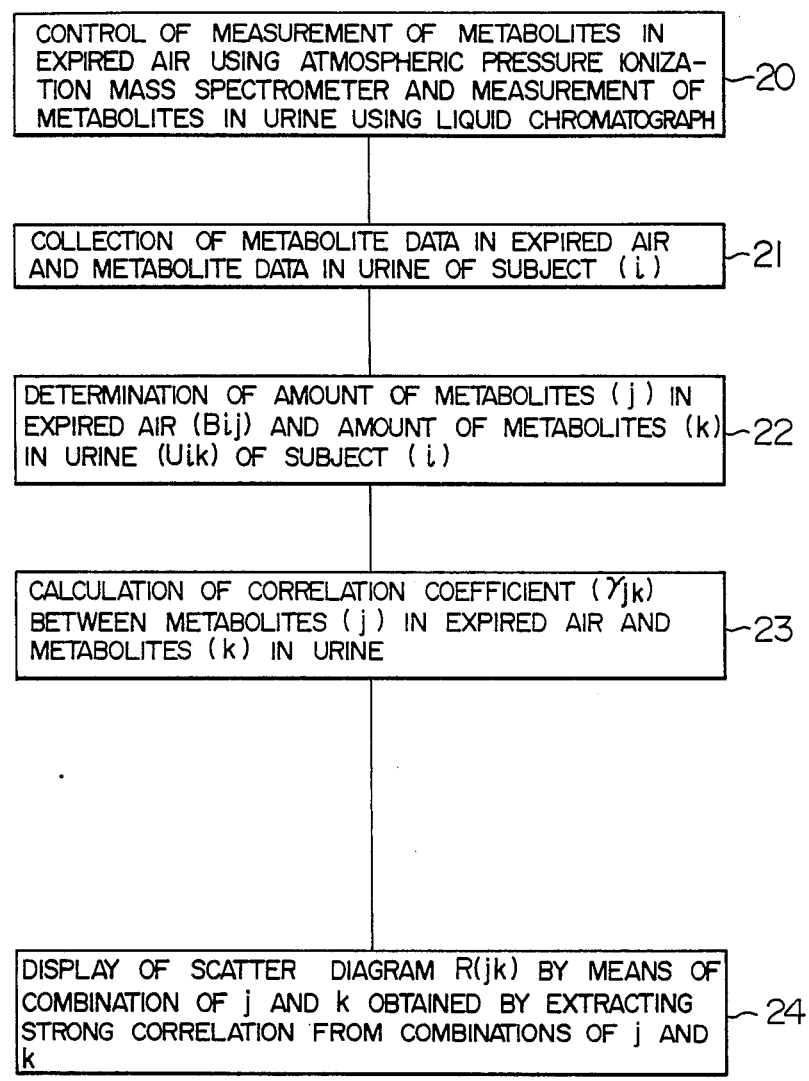
FIG. 2 is a flow chart showing one example of operations of the computer system 4 in FIG. 1.

The atmospheric pressure ionization mass spectrometer 1 and the liquid chromatograph 2 thus constituted are controlled by the computer system 4, respectively. The role of the computer system 4 is illustrated referring to FIG. 2 showing a flow chart.

First, an expired air sample and a urine sample of a subject (i) are measured by the atmospheric pressure ionization mass spectrometer 1 and the liquid chromatograph 2 under the control of the computer system 4 in the step 20. In the step 21, the measured data are acquired to the computer system 4 on-line via the interface 3. In the step 22, the amounts of metabolites (j) in the expired air (Bij) are determined from the expired air data of the subject (i) collected. In a similar manner, the amounts of metabolites (k) in the urine (Uik) are determined. In the step 23, correlation between the metabolites (j) in the expired air and the metabolites (k) in the urine is checked (calculation of a correlation coefficient $\gamma_{jk}$) by the computer system 4 in order to fine information which cannot obtained by the expired air sample data alone and the urine sample data alone.

The correlation coefficient $\gamma_{jk}$ is calculated by the following equation:

$$\gamma_{jk} = S(BjUk)/ \sqrt{S(BjBj) S(UkUk)} \text{ wherein}$$

$$S(BjBj) = \sum_{i=1}^{n} Bij^2 - \left\{ \left( \sum_{i=1}^{n} Bij \right)^2 /n \right\},$$

$$S(UkUk) = \left\{ \sum_{i=1}^{n} Uik^2 - \left( \left( \sum_{i=1}^{n} Uik \right)^2 /n \right) \right\}, \text{ and}$$

$$S(BjUk) = \sum_{i=1}^{n} Bij \, Uik - \left\{ \left( \sum_{i=1}^{n} Bij \sum_{i=1}^{n} Uik \right)/n \right\}.$$

In practice, there are detected several hundred peaks in the expired air spectrum obtained by the atmospheric pressure ionization mass spectrometer 1 (the value of j has several hundred ones). There are also detected several hundred peaks in the urine spectrum obtained by the liquid chromatograph 2 (the value of k has several hundred ones). Therefore, in order to check the correlation between these numerous peaks, it is very difficult to compute without using a computer. Further, when the number of subjects (i) increases, the calculation becomes almost impossible.

In the step 24, the degree of correlation between the metabolites in the expired air (j) and the metabolites in the urine (k) obtained by the computer system 4 is displayed, and if required, a scatter diagram R(jk) obtained by extracting data particularly having strong correlation can be displayed on a display device 25.

Figure 3:
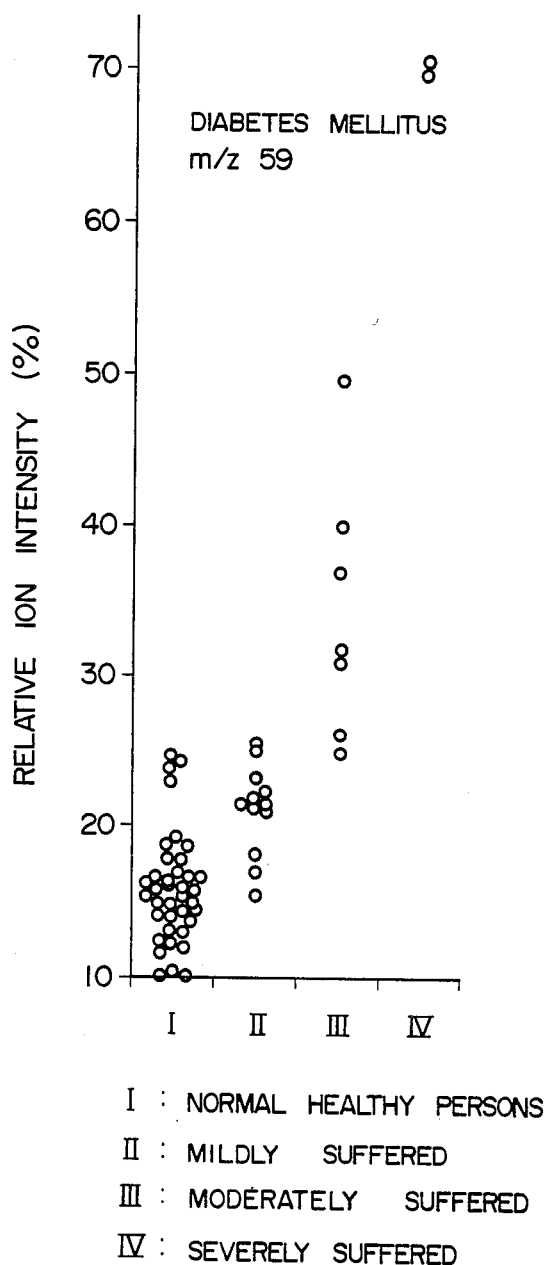
FIG. 3 is a graph showin a relationship between the concentration of acetone in expired air of healthy persons and subjects suffering from diabetes mellitus.

According to this invention, the following effects can be obtained. When the human expired air is analyzed by the atmospheric pressure ionization mass spectrometer 1 which is one constituent of the apparatus of this invention, acetone which is a trace amount metabolite (in a concentration of 10 ppb to several hundreds ppb in the human expired air) can be detected. FIG. 3 shows acetone concentrations in expired air of normal healthy persons (persons showing no abnormality in a usual medical examination) and subjects suffering from diabetes mellitus. The acetone concentration in the expired air of the subjects suffering from diabetes mellitus is higher than that of the normal healthy persons. This is because in the case of the diabetes mellitus, the decomposition of lipids is activated by the lack of sugars in the body, and as a result, the concentration of ketone body in the blood increases, which results in including acetone in expired air in lungs, the acetone being a volatile substance in the ketone body. As mentioned above, it is possible to diagnose diabetes mellitus non-invasively by the atmospheric pressure ionization mass spectrometer 1 without sampling blood and without putting a burden on a subject.

But sometimes the acetone concentration in the expired air of normal healthy persons is as high as that of subjects mildly suffering from diabetes mellitus as shown in FIG. 3. Such a case can be admitted on about 10% of total normal healthy persons examined. Such a value is very large from the medical point of view. In order to achieve a more correct, such a case should be distinguished from the diabetes mellitus.

In order to attain such an object, metabolites in the urine of such subjects are measured by the liquid chromatograph 2 and at the same time the acetone in the expired air is measured by the atmospheric pressure ionization mass spectrometer 1, and the correlation between the acetone in the expired air and the metabolites in the urine is examined by the computer system 4 with the following results. That is, even in the case of normal healthy persons, when the acetone concentration in the expired air is high, the amount of catechol amines (adrenaline and noradrenaline) in the urine increases (see FIGS. 4 and 5). On the other hand, when the same measurement is carried out as to the subjects suffering from diabetes mellitus, there is no correlation between the acetone in the expired air and the catechol amines in the urine. These results show that it is possible to distinguish the example of high acetone concentration in the expired air of normal healthy persons from the example of diabetes mellitus non-invasively, which provides an improved diagnosis.

An important finding in these results is a new finding that a cause for increasing the amount of acetone in the expired air of even normal healthy persons (excluding the influence of meals, fatigue, etc.) relates to the catechol amines. No report has been made as to the relation between the catechol amines in the urine and the acetone in the expired air and the present inventors have found this fact for the first time.

Figure 4:
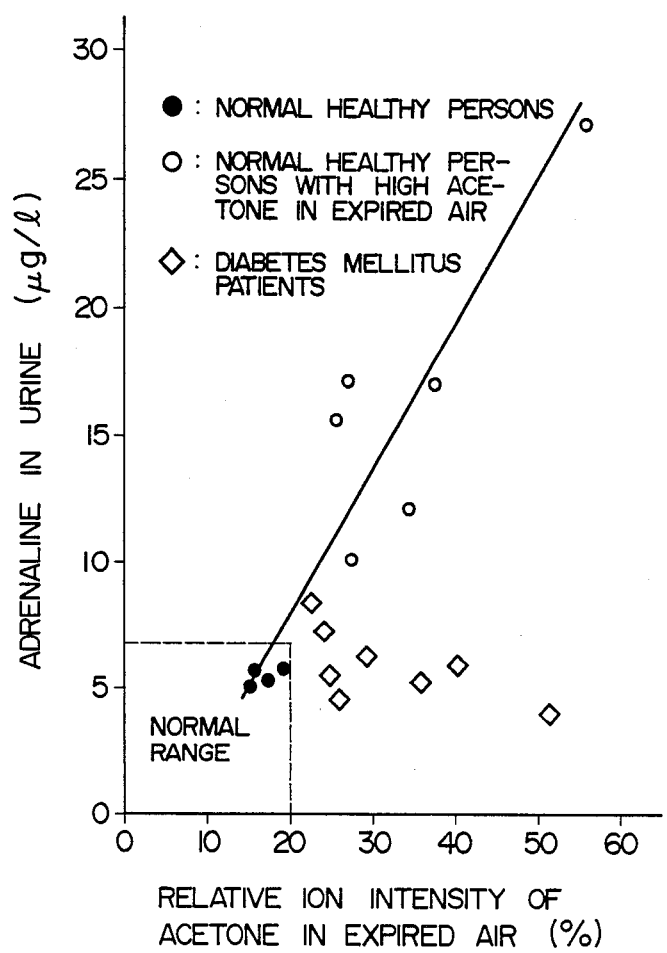
FIGS. 4 and 5 are graphs showing a relationship between acetone in expired air and adrenaline or noradrenaline which is a metabolite in the urine.
Figure 5:
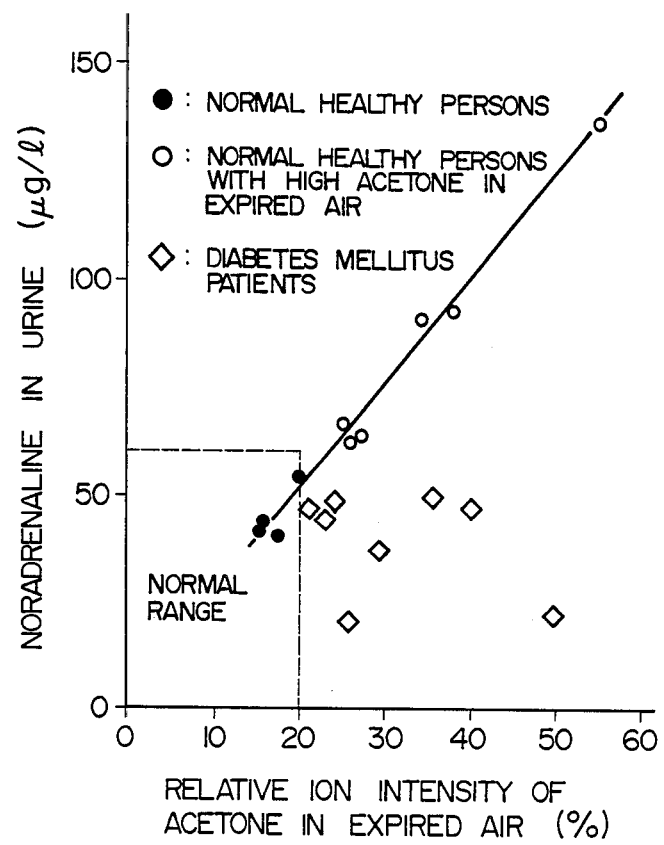

Catechol amines are secreted from the adrenal body under a tension state and are substances which can cause arterial sclerosis of a heart. Usually, the catechol amines are transient. But the examples wheren the amount of acetone in the expired air is large even in the case of normal healthy persons as shown in FIGS. 3, 4 and 5 are examples wherein the amount of acetone in the expired air is always large even when measured for a long period of time of one year. Thus the fact that catechol amines are continuously secreted in large amounts for such a long period of time seems to be one cause for heart disease. Therefore, by carrying out the above-mentioned measurement on normal healthy persons periodically, such a measurement can be one means of preventive medicine for the heart disease. Usually, normal healthy persons have a strong tendency to dislike the taking of blood samples, but, the above-mentioned measurement reduces the burden of subjects compared with conventional blood sampling and, thus, makes such subjects more agreeable to the test.

As mentioned above, by using the apparatus of this invention, the strong correlation between the acetone in the expired air and the adrenaline and noradrenaline in the urea can be grasped. Further, it is also possible to grasp relations among various substances by measuring a number of subjects in various states. This invention is effective not only in providing novel information in the medical field but also in applying the apparatus in practical diagnosis as mentioned below.

Figure 6:
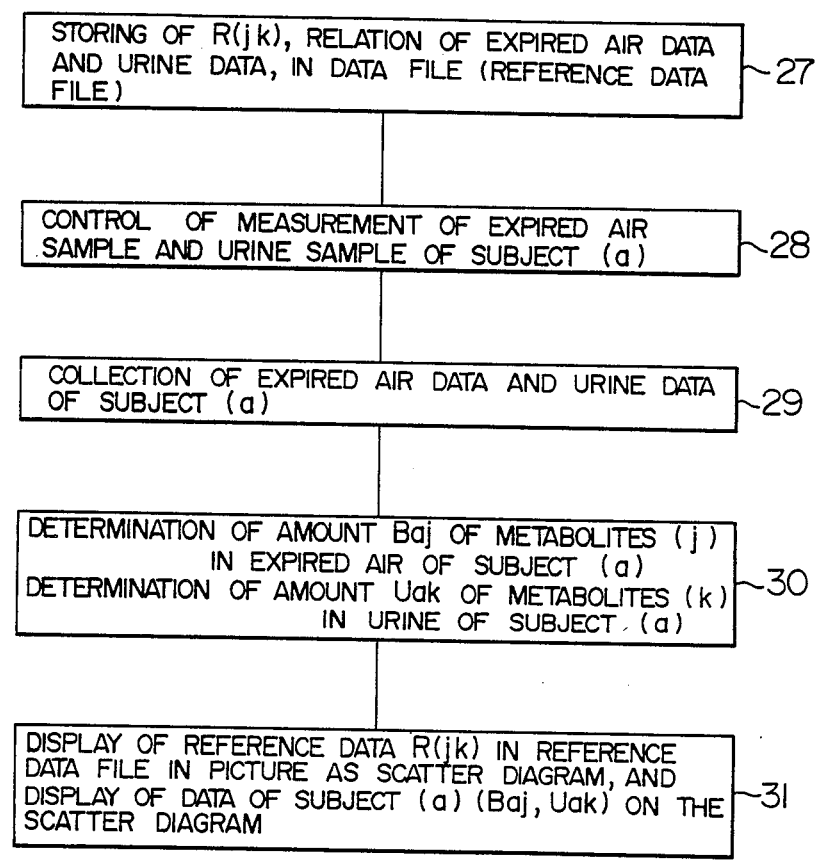
FIG. 6 is a flow chart showing another example of operations of the computer system 4 in FIG. 1.

The apparatus used for practical diagnosis is explained referring to FIG. 1 and the flow chart of FIG. 6. As shown in the step 27 in FIG. 6, new information data as shown in FIGS. 4 and 5 are stored in a data file 26 shown in FIG. 1 as reference data R(jk). In the step 28, an expired air sample and a urine sample of a subject (patient) a are measured, expired air data and urine data are collected in the step 29, and the amounts of metabolites j in the expired air (Baj) and the amount of metabolites k in the urine (Uak) are determined in the step 30. In order to know whether the data of the patient a (Baj, Uak) are normal or abnormal, comparison is made between the reference data R(jk) stored in the data file 26 and the measured data (Baj, Uak). This can be done, for example, as shown in the step 31, wherein the reference data R(jk) are displayed on the display device 25 as a scatter diagram and the measured data (Baj, Uak) are plotted on the displayed reference data. By doing this, differences between the reference data and the patient data can be readily seen. Then, medical doctors can decide upon a diagnosis and treatment for the patient.

In the above explanations, the atmospheric pressure ionization mass spectrometer is used as a device for measuring the metabolites in the expired air, but is is possible to use a gas chromatograph for measuring volatile metabolites in the expired air. The sensitivity of the gas chromatograph is not as good, but the cost can be reduced remarkably. In addition, it is possible to use a gas chromatograph or the same atmospheric pressure ionization mass spectrometer as used for measuring the metabolites in the expired air as a device for measuring the metabolites in the urine in order to measure volatile substances in the urine.

As constituent elements of the apparatus of this invention, it is possible to use a gas chromatograph-mass spectrometer (GC-MS) for measuring metabolites in the expired air and urine other than mentioned above. Further, it is possible to use an electrophoretic device for measuring the metabolites in the urine.

As mentioned above, according to this invention, the metabolites in the urine and the metabolites in the expired air can be measured at the same time, and the relationships among individual metabolites can be studied for comparison, so that new phenomena heretofore not known as to the metabolism can be determined. Further, the apparatus of this invention does not put a burden on a subject. Therefore, short interval tests as to the diagnosis and remedy for various diseases such as diabetes mellitus, heart disease, etc. become possible compared with the conventional blood tests.

What is claimed is:
1. An apparatus for parallel analysis of metabolites in human urine and expired air comprising
   means for measuring expired air to determine metabolites in the expired air of a person to be examined,
   means for measuring urine to determine metabolites in the urine of the person to be examined which is substantially simultaneously sampled with the sampling of the expired air of the person;
   means for storing data of metabolites in the expired air measured by the expired air measuring means and data of metabolites in the urine measured by the urine measuring means, and correlation extracting means for generating a correlation between the metabolites in the expired air and the metabolites in the urine from the metabolites data.

2. An apparatus according to claim 1, wherein the urine measuring means is a liquid chromatograph.

3. An apparatus according to claim 1, wherein the expired air measuring means has a sample concentrating means for concentrating the expired air sample gas.

4. An apparatus according to claim 1, wherein the expired air measuring means includes means for measuring volatile metabolites contained in the expired air and provides output data indicative thereof, and the urine measuring means includes means for measuring non-volatile metabolites contained in the urine and provides an output indicative thereof, the correlation extracting means generating a correlation between the volatile metabolites in the expired air and the non-volatile metabolites in the urine.

5. An apparatus according to claim 1, wherein the expired air measuring means includes means for measuring acetone in the expired air and provides output data indicative thereof, and the urine measuring means includes means for measuring catechol amine in the urine and provides output data indicative thereof, the correlation extracting means generating a correlation between the measured acetone in the expired air and the measured catechol amine in the urine of the person.

6. An apparatus according to claim 1, wherein the correlation extracting means includes means for calculating a correlation coefficient for the measured metabolites of the expired air and the urine of the person.

7. An apparatus according to claim 1, wherein the expired air measuring means is an atmospheric pressure ionization mass spectrometer comprising an ion source for ionizing an expired air sample udner an atmospheric pressure and a high vacuum portion having a mass analyzer and an ion collector disposed therein.

8. An apparatus according to claim 7, wherein the atmospheric pressure ionization mass spectrometer further comprises an intermediate pressure portion disposed between the ion source and the high vacuum portion.

9. An apparatus for parallel analysis of metabolites in human urine and expired air comprising:

means for measuring expired air to determine metabolites contained in the expired air from a subject, means for measuring urine to determine metabolites in the urine from the subject simultaneously sampled with the expired air, means for storing metabolites data determined from the measured expired air and the measured urine of the subject and for storing reference data showing a relation between the metabolites in the expired air and the metabolites in the urine, and comparison means for comparing a relation between the subject metabolites data in the expired air determined by the expired air measuring means and the subject metabolites data in the urine determined by the urine measuring means with the stored reference data showing the relation between the metabolites in the expired air and the metabolites in the urine so as to detect an abnormality of the subject.

10. An apparatus according to claim 9, wherein the expired air measuring means is an atmospheric pressure ionization mass spectrometer comprising an ion source for ionizing an expired air sample under an atmosphere pressure, a high vacuum portion having a mass analyzer and an ion collector disposed therein and an intermediate pressure portion disposed between the ion source and the high vacuum portion.

11. An apparatus according to claim 9, wherein the expired air measuring means includes means for measuring volatile metabolites in the expired air and provides output data indicative thereof, and the urine measuring means includes means for measuring non-volatile metabolites in the urine and provides output data indicative thereof, the storing means includes means for storing reference data showing a relation between the volatile metabolites in the expired air and the non-volatile metabolites in the urine, and the comparison means includes means for displaying the stored reference data showing the relation between the volatile metabolites in the expired air and the non-volatile metabolites in the urine stored in the storing means in the form of a scatter diagram and for displaying the stored subject metabolites data in the expired air and in the urine of the subject on the same displayed scatter diagram.

12. An apparatus according to claim 9, wherein the expired air measuring means includes means for measuring acetone in the expired air and provides output data indicative thereof, and the urine measuring means includes means for measuring catechol amine in the urine and provides output data indicative thereof, storing means storing reference data showing a relation between acetone in the expired air and the catechol amine in the urine, and said comparison means detects an abnormality by enabling comparison of a relation between the stoned subject metabolite output data of acetone in the expired air from said expired air measuring means and output data of the catechol amine in the urine from the urine measuring means with the stored reference data showing the relation between the acetone in the expired air and the catechol amine in the urine.

13. An apparatus according to claim 9, wherein the comparison means includes display means for displaying the stored reference data showing the relation between the metabolites in the expired air and the metabolites in the urine stored in the storing means in the form of a scatter diagram and for displaying the stored subject metabolite data in the expired air and in the urine on the same displayed scatter diagram.

14. An apparatus according to claim 9, wherein the comparison means includes means for calculating a correlation coefficient for the metabolite data from the expired air measuring means and the urine measuring means.

15. An apparatus for parallel analysis of metabolites in human urine and expired air comprising:

expired air measuring means for measuring acetone in an expired air from a subject;

urine measuring means for measuring catechol amine contained in the urine of the subject which is sampled at the time of sampling the expired air of the subject;

storing means for storing data of measured acetone and measured catechol amine of the subject and for storing reference data showing a relation between the acetone contained in the expired air and the catechol amine contained in the urine as to diabetes; and comparison means for comparing stored subject data of the acetone in the expired air detected by the expired air measuring means and the catechol amine in the urine detected by the urine measuring means with the stored reference data showing a relation between the acetone in the expired air and the catechol amine in the urine so as to detect an abnormality of the subject.

* * * * *